(12) United States Patent
Ansmann et al.

(10) Patent No.: US 6,828,468 B2
(45) Date of Patent: Dec. 7, 2004

(54) PREPARATION OF HIGHER α, β-UNSATURATED ALCOHOLS

(75) Inventors: Andreas Ansmann, Wiesloch (DE); Jochem Henkelmann, Mannheim (DE); Alois Kindler, Grünstadt (DE); Heinz Etzrodt, Neustadt (DE); Carsten Oost, Bad Dürkheim (DE); Susanne Stutz, Weinheim (DE); Christian Tragut, Brasschaat (BE); Bernhard Bockstiegel, Römerberg (DE); Klaus Reimer, Mutterstadt (DE); Manfred Stroezel, Ilvesheim (DE); Walter Dobler, Schwetzingen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 158 days.

(21) Appl. No.: 10/138,338

(22) Filed: May 6, 2002

(65) Prior Publication Data

US 2002/0183565 A1 Dec. 5, 2002

(30) Foreign Application Priority Data

May 11, 2001 (DE) ........................................ 101 23 066

(51) Int. Cl.$^7$ .............................................. C07C 33/04
(52) U.S. Cl. ...................... 568/874; 568/875; 568/885; 568/909.5
(58) Field of Search ................................ 568/874, 875, 568/885, 909.5

(56) References Cited

U.S. PATENT DOCUMENTS

| | | | | |
|---|---|---|---|---|
| 2,471,134 A | | 5/1949 | Wright | 196/100 |
| 2,795,617 A | | 6/1957 | Kimel et al. | 260/595 |
| 2,839,579 A | | 6/1958 | Kimel et al. | 260/595 |
| 3,023,246 A | | 2/1962 | Pasedach et al. | 260/595 |
| 3,283,014 A | | 11/1966 | Balducci et al. | 260/638 |
| 4,173,588 A | | 11/1979 | Pasedach et al. | 260/595 |
| 4,179,579 A | * | 12/1979 | Fujita et al. | 568/840 |
| 4,230,533 A | | 10/1980 | Giroux | 203/1 |
| 4,310,705 A | | 1/1982 | Nissen et al. | 568/391 |
| 6,300,524 B1 | | 10/2001 | Oost et al. | 568/406 |
| 6,307,106 B1 | | 10/2001 | Oost et al. | 568/406 |

FOREIGN PATENT DOCUMENTS

| | | |
|---|---|---|
| CH | 342 947 | 1/1960 |
| CZ | 216 360 | 7/1984 |
| DE | 1 053 498 | 3/1959 |
| DE | 1 068 696 | 11/1959 |
| DE | 1 078 112 | 3/1960 |
| DE | 1 232 573 | 1/1967 |
| DE | 26 52 863 | 5/1978 |
| DE | 29 28 944 | 2/1981 |
| DE | 35 22 234 | 1/1987 |
| DE | 42 20 239 | 12/1993 |
| DE | 19635703 | 3/1998 |
| DE | 19907532 | 8/2000 |
| EP | 0 122 367 | 10/1984 |
| EP | 0 126 288 | 11/1984 |
| EP | 0 133 510 | 2/1985 |
| EP | 0 412 415 | 2/1991 |
| EP | 0 564 830 | 10/1993 |
| EP | 0 780 147 | 6/1997 |
| EP | 0 816 321 | 1/1998 |
| EP | 827 944 | 3/1998 |
| EP | 0 983 988 | 3/2000 |
| EP | 1 000 922 | 5/2000 |
| EP | 1 008 582 | 6/2000 |
| FR | 1219166 | 5/1960 |
| GB | 788302 | 2/1955 |
| GB | 1101624 | 1/1966 |

OTHER PUBLICATIONS

Kurum, J. Chem. Tech. Biotechnol., vol. 70, pp. 29–44 (1997).*

Baerns et al. "Chemische Reaktionstechnik" (1992) pp. 328–330, no translation.

M. F. Carroll " Addition of βγ–Unsaturated Alcohols to the Active Methylene Group " J. Chem Soc. (1941) pp. 507–511.

M. F. Carroll " Addition of βγ–Unsaturated Alcohols to the Active Methylene Group " J. Chem Soc. (1940) pp. 704–706.

* cited by examiner

Primary Examiner—Michael L. Shippen
(74) Attorney, Agent, or Firm—Keil & Weinkauf

(57) ABSTRACT

Higher α,β-unsaturated alcohols are prepared by monoethynylation of a ketone by the NH$_3$/KOH method, if desired hydrogenation of the acetylene alcohol in the presence of hydrogen over a Pd-containing thin layer catalyst, purifying distillation of the hydrogenation product, preferably in a dividing wall column with recirculation of the unreacted ketone to the ethynylation step, and, if desired, preparation of higher alcohols having in each case 5 more carbon atoms in the chain by reacting the alcohols prepared by monoethynylation and, if desired, partial hydrogenation with alkyl acetoacetates diketene in a Carroll reaction to form ketones and using these as starting materials for the steps ethynylation, optional hydrogenation and fractional distillation.

17 Claims, No Drawings

PREPARATION OF HIGHER α, β-UNSATURATED ALCOHOLS

The present invention relates to a process for preparing higher α,β-unsaturated alcohols by monoethynylation of a ketone by the $NH_3$/KOH method, if desired hydrogenation of the acetylene alcohol in the presence of hydrogen over a Pd-containing thin layer catalyst, purifying distillation of the hydrogenation product, preferably in a dividing wall column with recirculation of the unreacted ketone to the ethynylation step, and, if desired, preparation of higher alcohols having in each case 5 more carbon atoms in the chain by reacting the alcohols prepared by monoethynylation and, if desired, partial hydrogenation with alkyl acetoacetatesor diketene in a Carroll reaction to form ketones and using these as starting materials for the steps ethynylation, optional hydrogenation and fractional distillation.

The continuously operated ethynylation of ketones with acetylene in liquid ammonia using catalytic amounts of base (usually KOH or potassium methoxide in a polar, protic solvent; 10–40° C.; 20 bar), e.g. as described in DE 1232573, is prior art.

In general, the $NH_3$/KOH process selectively gives the monoacetylene alcohol. The recirculation of the solvent $NH_3$ and of unreacted acetylene are likewise prior art. They are indispensable for the economics of the step.

The work-up of the reaction mixtures obtained by neutralization with water/$CO_2$ and subsequent phase separation/drying is likewise conventional prior art.

The continuously operated hydrogenation of alkynes and alkynenes over impregnated thin layer catalysts based on Pd/Ag and the production of these catalysts is described in EP 827 944. As regards hydrogenation using other catalysts or processes, reference may be made to the prior art disclosed in EP 827 944.

A number of process variants are customary for the continuous fractional distillation of multicomponent mixtures. In the simplest case, the feed mixture is separated into 2 fractions, namely a low-boiling fraction taken off at the top and a high-boiling bottom fraction. In the fractionation of feed mixtures to give more than 2 fractions, a plurality of distillation columns have to be used in this process variant. To limit the number of apparatus items required, columns in which liquid or gaseous streams are taken off at side offtakes are used where possible in the fractionation of multicomponent mixtures. However, the ability to employ distillation columns having side offtakes is greatly restricted by the fact that the products taken off at the side offtakes are never completely pure. In the case of streams taken off at side offtakes in the enrichment section, which are usually in liquid form, the side product still contains proportions of low-boiling components which are supposed to be separated off via the top. An analogous situation applies to streams taken off at side offtakes in the stripping section, which are usually gaseous, in which case the side product still contains high-boiling components. The use of conventional side offtake columns is therefore restricted to cases in which contaminated side products are acceptable.

A possible remedy is provided by dividing wall columns. This type of column is described, for example, in U.S. Pat. No. 2,471,134; U.S. Pat. No. 4,230,533; EP 0 122 367; EP 0 126 288 and EP 0 133 510.

In contrast to side offtake columns, dividing wall columns allow side products to be taken off in pure form. In the middle region above and below the feed point and the side offtake, there is a dividing wall which seals the feed section off from the offtake section and prevents crossmixing of liquid and vapor streams in this part of the column. This reduces the total number of distillation columns required in the fractionation of multicomponent mixtures. Since this type of column is a simplification in terms of apparatus of thermally coupled distillation columns, it also has a particularly low energy consumption. A description of thermally coupled distillation columns, which may have a variety of configurations, may likewise be found in the abovementioned literature references. Compared to an assembly of conventional distillation columns, dividing wall columns and thermally coupled columns offer advantages in respect of energy consumption and capital costs and are therefore increasingly being used in industry.

Various regulation strategies have been described for regulating dividing wall columns and thermally coupled columns. Descriptions may be found in U.S. Pat. No. 4,230,533; DE 35 22 234 and EP-780 147.

The preferred variants for carrying out the Carroll reaction are described in EP 1000 922, EP 1008 582 and EP 0983 988.

The essential features of the preparation of unsaturated ketones by reaction of α,β-unsaturated alcohols with alkyl acetoacetates in the presence of organic aluminum compounds with elimination of the parent alcohol of the acetoacetate are already known. The uncatalyzed reaction between an unsaturated alcohol and an alkyl acetoacetate was described for the first time by M. F. Carroll [J. Chem. Soc. (London) 1940, pp. 704–706]. The range of uses and the mechanism of this reaction were reported in 1941 by the same author [J. Chem. Soc. (London) 1941, pp. 507–511].

A description of a process for preparing 6,10,14-trimethylpentadec-5-en-2-one by transesterification of ethyl acetoacetate with 3,7,11-trimethyldodec-1-en-3-ol in the presence of aluminum trialkoxides may be found in the French patent 1 219 166 (1959). In this process, the reactants and the catalyst are both placed in the reaction vessel and the reaction is carried out batchwise with the alcohol which is liberated being separated by distillation. This gives the desired ketone in a yield of 77% after a reaction time of about 10 hours. Both the relatively long reaction times and the low yields are unsatisfactory for an industrial synthesis.

A number of further patent documents in which different variants of this Carroll reaction are described are known. Thus, U.S. Pat. No. 2,795,617 (1957) or DE-B 1 053 498 (1959) or Swiss patent 342947(1959) states that "although it is generally neither necessary nor desirable, a solvent can be used to temper the exothermic reaction". According to these patent documents, the aluminum trialkoxide is added to the acetoacetate of the α,β-unsaturated alcohol and the mixture is refluxed while stirring vigorously, with yields of up to 80% being achieved. The corresponding acetoacetate has to be prepared in a preceding step.

In U.S. Pat. No. 2,839,579 (1958) or DE-C 1078112 (1960), it is reported that the reaction can be carried out in a solvent. The corresponding acetoacetate is prepared in a separate step by condensation of diketene with an appropriate unsaturated alcohol. DE-C 1 068 696 also states that the concomitant use of a solvent might be advantageous.

In all cases, the solvents mentioned are high-boiling solvents whose boiling points are far above the reaction temperature. The yields indicated in these patents are unsatisfactory for industrial use. Even the concomitant use of a high-boiling solvent generally results in no appreciable increases in yield and therefore leads to a reduction in the space-time yields. A considerable disadvantage is that a further process step is necessary for preparing the acetoacetate of the α,β-unsaturated alcohol, since this is associated with further costs.

A process for preparing 2-methyl-2-hepten-6-one is described in DE-B 2652863 (1978). Here, alkyl acetoacetate, methylbutenol and catalyst are placed in a reaction vessel fitted with a superposed fractionation column and a mixture of alkyl acetoacetate and methylbutenol are subsequently metered in. During the reaction, the alkyl acetoacetate content of the reaction mixture should be no more than 15% by weight in order to avoid secondary reactions. However, a disadvantage of this process is that simple introduction of alkyl acetoacetate into excess methylbutenol is not possible since the boiling point of methylbutenol is far below the reaction temperature. The use of a high-boiling solvent, on the other hand, reduces the space-time yield.

The Czech patent 216 '360 (1979) describes carrying out the Carroll reaction in a mixture of unsaturated ketone and methyl or ethyl acetoacetate with addition of the unsaturated alcohol in an amount which is exactly that required for the reaction. In this process, the carbon dioxide and a mixture of the unreacted unsaturated alcohol and methanol or ethanol are distilled off from the reaction mixture and the mixture of alcohols is fractionated continuously in an attached distillation column. The α,β-unsaturated alcohol, whose boiling point has to be below 180° C., is subsequently returned to the reaction. Yields of about 80% are achieved at reaction times of 8 hours. According to the patent, this procedure is advantageous because it is not possible to prevent the two lower-boiling components from being carried from the reaction mixture by entrainment with the carbon dioxide formed.

The coupling of a distillation column to the actual reactor system as described in this patent is not absolutely necessary since correct design of the reactor system can prevent entrainment of the α,β-unsaturated alcohol in the carbon dioxide. For example, DE 2 928 944 describes a process in which it is possible to separate only methanol and carbon dioxide and to keep the α,β-unsaturated alcohol in the reaction vessel. Thus, the attached distillation column results first and foremost in additional capital and energy costs. A further disadvantage is the restriction of the boiling point of the α,β-unsaturated alcohol to below 180° C., since most alcohols relevant to the synthesis of vitamin E boil at above 200° C.

In contrast to the abovementioned patent documents, DE 2 928 944 (1979) describes the use of a solvent whose boiling point lies between that of the acetoacetic ester used and that of the alcohol to be eliminated therefrom. This solvent is referred to as an "intermediate boiler". The use of 3-methyl-1-buten-3-ol as reactive intermediate boiler is described as a particularly advantageous embodiment, since reaction of this with the alkyl acetoacetate takes place as an additional desirable secondary reaction to give 2-methyl-2-hepten-6-one as further product of value. Advantages of the use of such an intermediate boiler are said to be increased product yields and shorter reaction times and thus high space-time yields. Reactor systems proposed are a still pot with superposed fractionation column for a batchwise reaction and a heated cascade of reactors for a continuous process.

However, the use of an intermediate boiler has the following disadvantages. When an inert intermediate boiler is used, the reactor volume available for the reactants is decreased, i.e. the space-time yield which can be achieved is unavoidably decreased.

On the other hand, the use of the reactive intermediate boiler 3-methyl-1-buten-3-ol leads to unavoidable coproduction of 2-methyl-2-hepten-6-one, which can be undesirable. Furthermore, the process is restricted to systems in which the α,β-unsaturated alcohol has a boiling point higher than that of the alkyl acetoacetate used.

EP 816 321 describes a process for preparing hexahydrofarnesylacetone (phytone) or isophytol via, inter alia, the steps ethynylation/partial hydrogenation of ketones and the Carroll reaction. The process disclosed there has the following disadvantages in the individual steps:

Quantitative conversion is obtained in the ethynylation, as a result of which only poor selectivities are achieved. The residence times of 2–10 h are very high, which leads to low space-time yields and the need for large reactors. The neutralization is carried out using ammonium sulfate, which results in additional salts in the wastewater.

The partial hydrogenation described likewise suffers from poor space-time yields and selectivities. In addition, it is complicated since a suspended catalyst is employed and the complete separation of this from the product poses considerable engineering difficulties.

In the embodiment described, the Carroll reaction likewise leads to selectivities and space-time yields which are low for an industrial process.

It is an object of the present invention to provide a process for preparing higher α,β-unsaturated alcohols which gives particularly high space-time yields and selectivities and is simple to carry out in engineering terms.

We have found that this object is achieved by a process for preparing higher, α,β-unsaturated alcohols of the formula Ia or Ib

(Ia)

(Ib)

where
$R^1$ is hydrogen or a $C_1$–$C_4$-alkyl radical,
$R^2$ is a group of the formula II,

(II)

hydrogen or a saturated, monounsaturated or polyunsaturated $C_1$–$C_{30}$-alkyl, cycloakylalkyl or cycloalkyl radical which may each be substituted by $C_1$–$C_4$-alkyl where
$R^3$ is hydrogen or a $C_1$–$C_4$-alkyl radical, the broken line can be an additional double bond and
n is 0 or from 1 to 6, by
a) base-catalyzed monoethynylation of a ketone of the formula $R^1$—CO—$CH_2$—$R^2$ in liquid ammonia ($NH_3$/KOH method or $NH_3$/MOR method), where $R^1$ and $R^2$ are as defined above,
b) if desired, subsequent hydrogenation of the acetylene alcohol of the formula Ib in the presence of hydrogen over a Pd-containing thin layer catalyst and
c) subsequent purifying distillation of the hydrogenation product and, if desired, d) reaction of the alcohol of the formula Ia or Ib

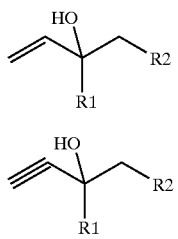

produced in steps a) to c) or a) and c) with diketene or alkyl acetoacetates of the formula IV

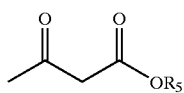

where $R^5$ is $C_1$–$C_4$-alkyl,
in the presence of from 0.1 to 0.5 mol % of an organic aluminum compound, based on the alkyl acetoacetate to be reacted, to produce the corresponding methyl ketone extended by 3 carbon atoms, e) and use of the ketone obtained in step d) as starting material for steps a) to wherein only a partial conversion of the ketone is achieved in step a) and the unreacted ketone is separated off in step c) and returned to step a).

The advantage of the process of the present invention lies in the combination of step a) with steps b) and/or c), and also, if desired, d) and e). This combination is of great economic value if the following conditions are adhered to in the individual steps:

In contrast to the prior art, the ethynylation of the ketone, step a), is carried out only to a partial conversion of from 50 to 95%, preferably from 75 to 85%. As a result, a particularly high selectivity of greater than 90%, preferably greater than 97%, is obtained. In particular, the formation of diols which occurs as a result of the secondary reaction of monoethynylated ketone with a further mole of ketone and reduces selectivity and product quality takes place only up to a content of 1%, preferably from 0 to 0.3%. This is of particular importance since the diols remain largely intact in step b) and are continuously dissociated into the acetylene alcohol and ketone in the subsequent distillation of c) and thus contaminate the allyl alcohol obtained. Especially in the further processing of isophytol with tnimethylhydroquinone to form vitamin E, dehydroisophytol leads to undesirable by-products.

The advantage of the high selectivity in the partial conversion is retained when the ethynyl compound present in the reaction mixture is, after neutralization with, preferably, carbon dioxide in water, reacted without purification by the method described, for example, in EP 827 944, step b), to form the corresponding allyl alcohol.

Here, the selectivity is surprisingly so high that the ketone present in the mixture remains virtually unchanged despite a concentration of from 5 to 50%, preferably from 15 to 25%, and the formation of the corresponding alcohols stays below 1%, preferably from 0 to 0.3%. These alcohols represent a loss of product and reduce the economic efficiency since they act as ballast and reduce the available capacity of the plant.

The crude hydrogenation product which is obtained from step b) and consists predominantly of allyl alcohol and ketone is fractionated by distillation in c) and the ketone which was not reacted in a) is separated off and returned to a). The value of the high selectivity obtained in a) and b) is increased when the ketone is obtained in high purity and is recirculated. Here, a low content of the corresponding alcohol as obtained in b) is essential. This can be separated off by distillation only incompletely and/or with a very high engineering outlay accompanied by loss of ketone, since it goes back together with the ketone to step a) where it accumulates as inert ballast and reduces the capacity of the plant. This would reduce the advantage of the high selectivities in a) and b) and decrease the economic utility of the process. Discharge of >5% of the recycled stream would, owing to the loss of ketone, reduce the advantage of the high selectivities of steps a) and b).

It is of great economic advantage to carry out the fractional distillation of the mixture obtained after a) and b) in a dividing wall column, e.g. as described in EP 0 122 367 or U.S. Pat. No. 2,471,134 since the necessary purity of allyl alcohol and ketone can be achieved in this way with a small outlay in terms of apparatus.

Regardless of the distillation method, it is particularly advantageous to separate the hydrogenation product from high-boiling components by means of a short path distillation prior to the fractional distillation and to feed the distillate which has been freed of high boilers into the side of the fractionation column. This is carried out at atmospheric pressure, but preferably under reduced pressure; it is advantageous to employ the lowest technically achievable and economically justifiable pressure. Short path distillation achieves the lowest possible pressure with a minimal pressure drop at the place where vaporization takes place since no internals which cause a pressure drop are necessary between the vacuum apparatus and the evaporation surface and sufficiently large pipe cross sections can be used. A reduced pressure of from 0.1 to 20 mbar, preferably from 1 to 2 mbar, can be achieved without problems. A particularly advantageous embodiment involves the simultaneous use of this short path evaporator for the removal of high boilers from the distillation bottoms from the fractionation column by feeding a substream of the distillation bottoms into the fresh feed to the short path evaporator and freeing them of the high boilers together. The particular advantage is that the distillation column has to cope only with components which can be vaporized under the distillation conditions and the boiling temperature at the bottom can be kept to a minimum. This is of particular economic advantage since, particularly in the case of high-boiling mixtures, the thermal stress can be minimized and the losses due to thermal decomposition or condensation to form high-boiling constituents can thus also be minimized. This applies particularly to the crude product from the hydrogenation of b) when 2-nerolidol, dihydronerolidol or tetrahydronerolidol is distilled in the presence of the ketones used in a); likewise to isophytol in the presence of the hexahydrofarnesylacetone used in a).

Subsequent combination with step (d) and use of the product from step (d) as starting material for step (e) is particularly advantageous according to the present invention since the ketone from step d) has, owing to the method described there, a particularly low content of the alcohol formed by Meerwein-Ponndorf-Verley reduction. The advantageous effects of this low alcohol content have already been described above for the combination of the steps a), b) and c). In addition, this low alcohol content makes the sequential buildup of longer allyl alcohols extended in each case by a pentan-2-on-5-ylidene group according to d) and e) particularly economically interesting since each desired alcohol extended by $C_5$, $C_{10}$, $C_{15}$ etc. is obtained in good yield in this sequence because of the low by-product formation.

The process can also be carried out so that an alcohol of the formula Ia or Ib which has been extended by a pentan-2-on-5-ylidene group is obtained in the sequence of steps d) and e).

The invention further provides a process for preparing an alcohol of the formula Ia in which only the steps a) to c) are carried out.

In a further variant of the process of the present invention, the acetylene alcohol of the formula Ib obtained in step a) is subjected directly, with step b) being bypassed, to the purifying distillation of step c). A further reaction according to steps d) and e) can subsequently be carried out.

However, the preferred variant of the process of the present invention is preparation of an allyl alcohol of the formula Ia by means of the reaction of steps a) to e), with the sequence of steps a) to e) also being able to be carried out a plurality of times.

In the process of the present invention, $R^2$ is preferably a group of the formula II

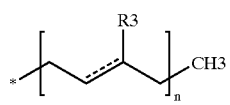
(II)

For the purposes of the present invention, a $C_1$–$C_4$-alkyl radical is a methyl, ethyl, propyl, i-propyl, butyl or t-butyl radical.

A cycloalkyl radical is, for the present purposes, a 3- to 7-membered ring which may be monounsaturated or polyunsaturated, for example a cyclopropyl, cyclobutyl, cyclopentyl, cyclohexyl or cycloheptenyl radical.

For the purposes of the present invention, a cycloalkylalkyl radical is a cycloalkyl radical bound via a $C_1$–$C_{30}$-alkyl radical.

The process can be carried out either continuously or batchwise. However, preference is given to carrying it out continuously.

Higher α,β-unsaturated alcohols of the formula Ia are allyl alcohols while the alcohols of the formulal Ib are propargyl alcohols. The process of the present invention is preferably used for preparing allyl alcohols of the formula Ia.

Preference is given to preparing the allyl alcohols employed as intermediates for the preparation of the essential vitamin E precursor isophytol and the allyl alcohols which are sought after as fragrances and flavors, for example 3,7,11-trimethyl-1,6,10-dodecatrien-3-ol (2-NER), 3,7,11-trimethyl-1,6-dodecadien-3-ol (HNER), 3,7,11-trimethyldodec$^{-1}$-en-3-ol (THNER), 3,7,11,15-tetramethyl-1-hexadecen-3-ol (IP), 3,7-dimethylocta-1,6-dien-3-ol (2-LIN), 3,7-dimethyloct-1-en-3-ol (HLIN), 3-methyl-1-(2,6,6-trimethyl-1-cyclohexen-1-yl)penta-1,4-dien-3-ol, 3-methyl-3-hydroxybutene (MBE), or the acetylene alcohols 3,7,11-trimethyldodec-1-yn-3-ol (TMD), 3,7,11,15-tetramethylhexadec-1-yn-3-ol (DIP), 3,7,11-trimethyl-6,10-dodecadien-1-yn-3-ol (2-DHNER), 3,7,11-trimethyl-6-dodecen-1-yn-3-ol (DHNER), 3,7-dimethyloct-6-en-1-yn-3-ol (2-DHL), 3,7-dimethyloct-1-yn-3-ol (HDHL), 3-methyl-1-(2,6,6-trimethyl-1-cyclohexen-1-yl)penta-4-en-1-yn-3-ol, 3-methyl-3-hydroxybutyne (MBI), particularly preferably the alcohols 3,7,11-trimethyldodec$^{-1}$-yn-3-ol (TMD), 3,7,11,15-tetramethylhexadec-1-yn-3-ol (DIP), 3,7,11-trimethyldodec-1-en-3-ol (THNER), 3,7,11-trimethyl-1,6,10-dodecatrien-3-ol (2-NER), 3,7,11-trimethyl-6,10-dodecadien-1-yn-3-ol (2-DHNER) and 3,7,11,15-tetramethyl-1-hexadecen-3-ol (IP) with high selectivity, in high space-time yields and in a technically simple manner.

Furthermore, it is also possible to carry out the ethynylation of (a) using ketones which are obtained by partial or complete selective C=C hydrogenation of 6,10-dimethylundeca-3,5,9-trien-2-one (pseudoionone, PSI) or 6,10,14-trimethylpenta-5,9,13-trien-2-one (2-farnesylacetone).

Further examples of ketones of the formula IV, apart from the ketone used for preparing the abovementioned alcohols, are acetone, diethyl ketone, methyl ethyl ketone, cyclohexanone, methyl isobutyl ketone, methyl vinyl ketone.

In principle, all acetylene alcohols prepared by ethynylation in step a) can be hydrogenated selectively to the corresponding allyl alcohols.

The acetylene alcohols can be reacted in the hydrogenation as pure substances or as mixtures with one another. Furthermore, the presence of ketone which has not been reacted in step a) in admixture with the corresponding acetylene alcohol does not interfere in the hydrogenation, since the ketone is not attacked in the hydrogenation under the process conditions of the present invention even when it is present in a high concentration.

Dividing wall columns and thermally coupled columns are particularly useful for the fractional distillation of the reaction product from step a) and b) and step d) in the process of the present invention. In the work-up of the crude reaction product from step a) and b), the desired product, namely the allyl alcohol, is taken off in high purity via the side offtake of the column. The unreacted ketone is obtained at the top or at a side offtake located in the upper third of the column and is, if appropriate after bleeding off a substream, returned to step a). High-boiling by-products are discharged via the bottom of the column.

As an alternative, the dividing wall column can be provided with 2 side offtakes. In this way, by-products which have a boiling point between those of the desired product and low boilers or between those of the desired product and high boilers can be discharged in high concentration.

Thus, for example, in the preparation of H-nerolidol, the desired product can be taken off in a purity of above 98% via the side offtake. The unreacted H-geranylacetone is obtained at the top of the column and can be returned to step a). The high boilers are discharged via the bottom of the column. It is particularly advantageous to separate off the high boilers continuously from the bottoms from the distillation column in an external short path evaporator which is operated at a pressure lower than that in the distillation column. The distillate from the short path evaporator is returned to the dividing wall column. In this way, it is possible to achieve a minimal bottom temperature, which minimizes decomposition of desired product and increases the distillation yield.

The distillation in c) can also be carded out in two thermally coupled columns as an alternative to a dividing wall column. In the case of thermally coupled columns, it can be advantageous to vaporize part or all of the bottom stream from the first column in an additional vaporizer and then to pass it to the second column. This prevaporization is particularly useful in the present case because the bottom stream from the first column contains relatively large amounts of middle boilers. In this case, prevaporization can be carried out at a lower temperature and the load on the vaporizer of the second column can be decreased. Furthermore, this measure considerably reduces the load on the stripping section of the second column. The prevaporized stream can be fed to the second column either as a two-phase stream or in the form of two separate streams.

Furthermore, it can be advantageous, both in the case of dividing wall columns and in the case of thermally coupled columns, to subject the feed stream to a prevaporization and subsequently to feed it to the column as a two-phase stream or in the form of two streams. This prevaporization is particularly useful when the feed stream contains relatively large amounts of low boilers. In the present case, this occurs when conversions are low. The prevaporization can significantly reduce the load on the stripping section of the column.

Dividing wall columns and thermally coupled columns can be configured both as packed columns containing random packing or ordered packing or as tray columns. In the case of packed columns, ordered sheet metal packings having a specific surface area of from 100 to 500 m²/m³, preferably from about 250 to 300 m²/m³, are particularly useful.

The preparation of, for example, dehydrodihydronerolidol (DHNER) (step a)) and the other acetylene alcohols is preferably carried out continuously (20 bar, 20–50° C.; $NH_3$ (1) as solvent). It is particularly advantageous to carry out the ethynylation in a nonbackmixed tube reactor having plug flow characteristics. Such characteristics are ensured when the CSTR index (for definition, see Baerns, Hofmann, Renken, Chemische Reaktionstechnik, Lehrbuch der Technischen Chemie, Volume 1, $2^{nd}$ edition, Thieme Verlag Stuttgart 1992, pp. 328–330) is greater than 50. The reaction product is hydrolyzed and neutralized in a mixing apparatus such as a static mixer or a reaction mixing pump, as described in DE 4220239. Phase separation is carried out with the aid of a coalescing filter. The residual water is finally removed from the organic crude DHNER solution (reduction in water content from 1.5% by weight to <0.5% by weight) in a thin film evaporator operated under reduced pressure.

DHNER is formed from HGAC and acetylene in a single-stage reaction with the aid of catalytic amounts of base. The base, generally referred to as MOR, can consist of alkali metal hydroxides, dissolved in an aliphatic $C_1$–$C_8$-alcohol such as methanol, ethanol, propanol, i-propanol or butanol, preferably KOH in methanol, alkali metal alkoxides in the corresponding alcohol, preferably potassium methoxide in methanol or any primary, secondary or tertiary amine, but is preferably potassium methoxide in methanol.

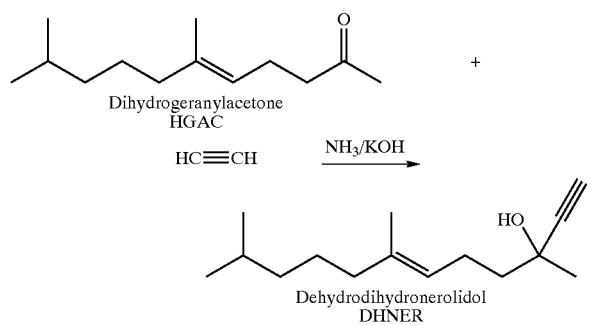

The ethynylation section comprises a tube reactor supplied with three liquid feed streams and one gaseous feed stream which are intimately mixed in a mixer. Ammonia, the ketone and the basic catalyst solution are fed continuously into the reactor.

Acetylene is metered into the reactor. It is particularly advantageous to carry out the reaction without a gaseous feed stream by dissolving the acetylene required in ammonia in an upstream separator and feeding it to the mixer as an ammoniacal solution. A further preferred embodiment comprises replacing the proportion of acetylene consumed by the reaction after a subsection of the reactor by feeding in further acetylene or acetylene dissolved in ammonia. The reaction takes place at a pressure of 20 bar and temperatures of about 20–50° C.

The molar ratio of the reactants is preferably as follows:

| Ketone mol:mol | Acetylene mol:mol | Base mol:mol | $NH_3$ mol:mol |
|---|---|---|---|
| 1 | 2.5–3.5 | 0.01–0.03 | 12–25 |

The conversion of ketone in the ethynylation can be complete, but it is particularly advantageous to allow only a partial conversion in the ethynylation.

The ammonia fed into the reaction and the acetylene not consumed in the reaction are recirculated. The ammonia and the acetylene are separated together from the reaction mixture by flash vaporization.

The offgas streams are collected and passed through an absorption column and a desorption column. In these columns, ammonia is separated from the offgas stream and the acetylene by means of water or lower glycols, e.g. ethylene glycol, and recovered in pure form by distillation, while the unconsumed acetylene is compressed again and returned to the reaction.

The degassed organic crude solution is metered into a mixing apparatus such as a static mixer or reaction mixing pump and neutralized. In this mixing apparatus, the crude product is intimately mixed with water and $CO_2$ and neutralized. This can be carried out under atmospheric pressure or under superatmospheric pressure. In the first case, a 3-phase mixture, namely organic phase, aqueous phase and gas phase, is present during the neutralization process, while under superatmospheric pressure the neutralization occurs in a 2-phase mixture, namely organic phase (liquid) and aqueous phase (liquid). The 2-phase process variant under superatmospheric pressure is preferably employed, since this makes the process easier to control and no appreciable excess of gas phase is necessary. The product mixture is separated into aqueous and organic phase. The organic phase is dewatered by passing it through a thin film evaporator and the residual water is taken off at the top. The dewatered product, which can comprise, for example, DHNER together with the unreacted ketone HGAC, is passed directly to the hydrogenation.

HNER is obtained in a single-stage reaction by reacting the DHNER with hydrogen over a Pd-containing thin layer catalyst (step b)). The ketone present in the feed is not attacked. The thin layer catalyst can be produced by vapor deposition, sputtering (EP564830, EP 412415) or preferably by impregnation (EP 827 944). As active components, those mentioned in EP 827 944 in the concentrations indicated there are useful. The external shape of the catalysts is likewise described in EP 827 944. To increase the selectivity, CO is mixed into the hydrogen.

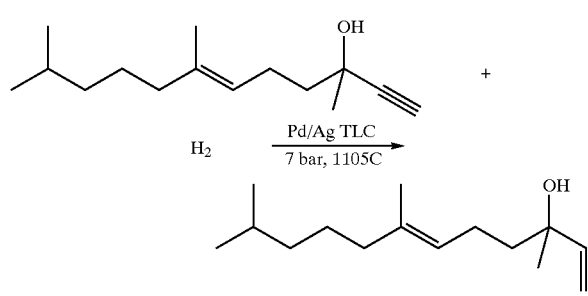

After reduction of the catalyst with hydrogen at from 20 to 250° C., preferably from 70 to 200° C., which is advantageously carried out in the reactor, the catalyst is ready to use for the partial hydrogenation of the present invention.

The catalysts used have not only good selectivity and activity but also a long operating life. This is a great advantage, especially for continuously operated single stream plants, since it minimizes shutdown times for frequent catalyst changes.

The conversion of the DHNER into HNER takes place in at least two reactors connected in series. In the first reactor and optionally in a further reactor provided with liquid circuit and gas circuit, from 90 to 95% of the conversion are achieved while the remaining conversion is achieved in a second reactor and optionally in a further reactor having plug flow characteristics. The feed to the second reactor is supplied from the gas/liquid separator in the circuit of the first reactor and the feed rate is level-regulated.

Setting the cross-sectional throughput of the gas and of the liquid in the first reactor in the range from 20 to 500 m$^3$/m$^2$ h, preferably from 100 to 300 m$^3$1 m$^2$*h, is advantageous for the hydrogenation. Each of the two reactors can also be installed in duplicate, with the component reactors each being able to be connected in series or in parallel.

For a partial hydrogenation on an industrial scale, it is particularly advantageous for the circulated gas to be injected into the reactor in very finely divided form by means of the liquid stream and a suitable apparatus such as a liquid/gas compressor. Together with the shaping of the catalyst monoliths and the above-described introduction of gas into the reactor, high space-time yields are achieved by optimal transverse mixing and good hydrodynamics at the catalyst surface. The partial hydrogenations are carried out, depending on the substance, at from 20 to 250° C., preferably from 60 to 200° C. The hydrogenation is operated at from 0.3 to 200 bar, preferably from 0.5 to 20 bar.

The supply of hydrogen and oxo gas (1:1 mixture of hydrogen and CO) to the two reactors is quantity-regulated. A contionubus IR measurement enables the CO content of the offgas stream to be determined. This value can be used to regulate the feed rate of oxo gas. The hydrogenation can be carried out particularly advantageously when the feed rate of CO is regulated via a conversion measurement. The CO contents of the hydrogen should be in the range from 10 to 2000 ppm, preferably from 300 to 1800 ppm, of CO. The CO in the liquid phase can also be allowed to form by slight decomposition of a compound which splits off CO mixed into the acetylene alcohol, provided that the abovementioned ranges for the CO concentration in the gas phase are not exceeded.

The output from the hydrogenation (b) is then passed directly to the work-up by distillation (step (c)).

The purifying distillation column is a packed column having a dividing wall and is operated at a pressure at the top of from 20 to 300 mbar, preferably 150 mbar.

The hydrogenated mixture is fed into the column at the side inlet. The low boilers, mainly unreacted ketone from step 2 (here HGAC), go over at the top and are condensed out in the condenser at the top or via the upper side offtake. The condensed vapors are collected and returned to the ketone reservoir for step (a). An opportunity for discharging it is provided. More advantageously, the ketone can be taken off in higher purity from the second side offtake in the upper region of the dividing wall column, with a small stream of low boilers being obtained at the top.

The purified HNER is taken off in liquid form at the side offtake in the region of the dividing wall.

Temperatures of not more than 200° C., preferably from 180° C. to 190° C., are reached in the bottom of the column. The bottom heat exchanger is operated using 16 bar steam.

At these temperatures, only small amounts of HNER are present in the bottoms. To separate off this HNER, the bottoms are fed to a thin film evaporator. The product taken off at the top of this is returned to the column. The bottoms from the thin film evaporator are discharged from the process.

If the H-NER obtained after steps a)–c) is subsequently reacted further according to step d) to produce H-farnesylacetone (6,10,14-trimethyl-5,9-pentadecadien-2-one), the preparation is advantageously carried out continuously at 500 mbar in a reaction column. The methanol and carbon dioxide formed are separated off at the top of the reaction column. The bottoms stream from the reaction column, which comprises the desired product together with high boilers, is worked up in a dividing wall column operated at 100 mbar. The bottoms from the dividing wall column are freed of remaining desired product in a downstream thin film evaporator and this desired product is returned to the column to increase the yield. Unreacted reactants are returned to the reaction column.

The H-farnesylacetone is prepared by reaction of H-NER with methyl acetoacetate (MAA) in a Carroll reaction in which methanol and carbon dioxide are formed as coproducts. Although the reaction can be carried out thermally, significantly higher yields are obtained in the presence of aluminum alkoxides or aluminum triacetoacetates.

The H-farnesylacetone synthesis is accompanied by, as a secondary reaction, a Meerwein-Ponndorf-Verley reduction in which the H-farnesylacetone isomers are reduced to the corresponding alcohols.

These H-farnesylacetonols are undesirable by-products. The Meerwein-Ponndorf-Verley reduction is catalyzed by aluminum alkoxides. For this reason, the use of aluminum triacetoacetates in the Carroll reaction is advantageous.

A further secondary reaction is the thermal dehydration of H-NER, which forms the various dimethyldodecadienes.

Apart from the abovementioned by-products, decomposition and downstream products of methyl acetoacetate are observed in the Carroll reaction. Thus, for example, acetone, methyl acetate and dehydroacetic acid are found.

The process of the present invention is preferably carried out by metering the reactants together with the catalyst into a fractionation column. In this case, it is advantageous for the higher-boiling reactant (H-NER) to be fed continuously into the fractionation column, either separately or together with the liquid catalyst, at a point above the lower-boiling reactant (MAA). The reaction together with a superimposed distillation then take place in the fractionation column. As a result, the carbon dioxide liberated during the reaction and the alcohol formed from the acetoacetic ester (methanol) are continually removed from the reaction mixture.

The carbon dioxide and the methanol leave the column together with the low boilers via the stream from the top and go to a condenser where the condensible constituents of the vapor stream are condensed out. Part of the condensate is returned to the column as runback and the other part is taken off. A reflux ratio of from 1 to 10, preferably from 2 to 4, should be set. However, it is also possible for all of the condensate to be taken off if the higher-boiling reactant is introduced at one of the uppermost stages. The pressure at the top of the column is set so that the temperature at the bottom is from 100 to 300° C., preferably from 180 to 220° C. Depending on the chemical system and the desired temperature at the bottom, this can be achieved by means of a vacuum pump and/or a regulating valve. The reaction product collects at the bottom of the column and is taken off together with the unreacted reactants (H-NER, MAA) via the bottoms stream by means of a pump. The crude product (H-farnesylacetone) is discharged by means of a regulating valve via the product line and is passed to further work-up.

The amounts metered in are chosen so that the stoichiometric ratio of the reactants is from 0.8 to 1.2, preferably from 0.95 to 1.05, and a catalyst content of from 0.1 to 5 mol %, preferably from 1 to 3 mol %, based on the alkyl acetoacetate to be reacted, is established. The residence time of the reaction mixture in the reactor system consisting of vaporizer and fractionation column should be from 15 minutes to 6 hours, preferably from 0.5 to 2 hours. To carry out the reaction, from 10 to 100 theoretical plates, preferably from 20 to 40 theoretical plates, are necessary. From 0 to 5 theoretical plates should be provided in the upper part of the column above the feed point and from 0 to 5 theoretical plates should be provided in the lower part of the column below the feed point.

In the work-up of the crude product stream, it is advantageous to separate off the catalyst first by means of a thin film evaporator, with a substream of the bottoms from the subsequent distillation columns or dividing wall columns preferably also being mixed into the inflow stream to separate off the high boilers formed in the column, and subsequently to isolate the desired product in downstream distillation columns.

Unreacted reactants (H-NER, MM) which are separated off in the downstream distillation columns or dividing wall columns can be returned to the reaction column.

Preference is given to using a dividing wall column from which H-NER and MM are taken off at the top, the H-farnesylacetone is taken off via a side offtake and the high boilers are separated off at the bottom. It is likewise possible to use a dividing wall column having 2 side offtakes. In this case, the desired product is taken off via the lower side offtake and the unreacted allyl alcohol H-NER is taken off via the upper side offtake.

As an alternative, the bottoms stream from the reaction column can be worked up directly in the dividing wall column. In this case, the bottoms should be conveyed into a downstream thin film evaporator in which the high boilers are separated off. The vapor stream from the thin film evaporator is recirculated to the dividing wall column. The H-farnesylacetone obtained in this way can then be used as starting material in step a) for further conversion into isophytol (step e)).

The invention is illustrated by the following examples without being restricted thereto:
Preparation of H-Nerolidol
Step (a): Ethynylation (Continuously Operated Plant)

Synthesis of dehydrodihydronerolidol (DHNER) by continuous ethynylation of hexageranylacetone (HGAC) by the $NH_3$/KOH method.

The reactor used is a 1.8 l stainless steel reactor having plug flow characteristics (reaction tube having a diameter of 6 mm).

In a start-up phase, 870 g/h of HGAC, 285 standard l/h of acetylene, 750 g/h of $NH_3$ and 58 g/h of potassium hydroxide solution in methanol (8.5 mol %) are pumped continuously into the reactor. The metering of all three streams into the reactor is quantity-regulated. The reaction temperature is maintained at from 25 to 35° C.

Of the HGAC metered in, about 190 g/h come from the recirculation from the distillation after the hydrogenation.

The residence time in the reactor is 42 minutes.

The discharge of the output from the reaction is pressure-regulated (20 bar +/−0.05 bar).

Degassing is carried out in three stages:
1. Flash pot at 90° C.; 1013 mbar
2. Thin film evaporator at 50° C.; 1013 mbar
3. Degasser at 40° C.; 150 mbar Neutralization and hydrolysis are carried out using 500 g/h of water and 10 standard l/h of $CO_2$ gas in a reaction mixing pump at 70° C. After phase separation in a coalescing filter (50 $\mu$m) at 70° C., the organic phase is dried in a further thin film evaporator operated at 90° C. and 150 mbar. 950+/−30 g/h of crude organic output (~15% by weight of unreacted HGAC and ~82% by weight of DHNER) are passed continuously to step 3 (hydrogenation). The aqueous phase comprises potassium hydrogen carbonate together with traces of ammonium hydrogen carbonate (>0.5 g/100 g).

Step (b): Hydrogenation
Production of the Catalyst

A smooth Kanthal mesh (material number 1.4767) having a mesh opening of 180 $\mu$m and a wire diameter of 112 $\mu$m is heated at 950° C. for 5 hours in air. A 20 cm wide strip of mesh was clamped to a winding apparatus and subsequently transported continuously through an impregnation bath containing an aqueous metal salt solution of palladium nitrate and silver nitrate. The subsequently dried mesh strip was coated with 280 mg of $Pd/m^2$ and 70 mg of $Ag/m^2$. The catalyst intermediate product was activated at 300° C. for 3 hours in an electric muffle furnace. The fabric was subsequently corrugated, rolled up and thus made into monoliths.

Continuous selective hydrogenation of dehydrodihydronerolidol (3,7,11-trimethyl-6-dodecen-1-in-3-ol) to dihydronerolidol (3,7,11-trimethyl-1,6-dodecadien-3-ol)

4 metal monoliths having a diameter of 35 mm and a height of 200 mm and one monolith having a diameter of 35 mm and a height of 100 mm were installed in the first tube reactor of the plant. A second tube reactor was provided with 4 monoliths having a diameter of 27 mm and a height of 200 mm. The first reactor was operated in the upflow mode with recirculation at a cross-sectional liquid throughput of 200 $m^3/m^2*h$ and a cross-sectional hydrogen throughput of 200 $m^3/m^2*h$ at a total pressure of 7 bar. The circulated gas was injected into the reactor via a jet nozzle. CO was added to the hydrogen in such an amount that the CO concentration in the offgas, whose composition corresponds to that of the circulated gas, was from 1200 to 1500 ppm. The temperature in the first reactor was 115° C. The amount of crude organic output which was fed in was 950+/−30 g/h. The second reactor is operated in the upflow mode in a single pass at a pressure of 4 bar, a temperature of 91° C. and a CO concentration in the hydrogen of 225 ppm. The feed rate to the second reactor is regulated via the level in the gas/liquid separator in the circuit of the first reactor. The output from the second reactor is passed continuously to the work-up by distillation. The output comprises about 15% by weight of unreacted HGAC from step 2, about 78.5% by weight of HNER, 2% of unknown high-boiling components and 1% of tetrahydronerolidol (overhydrogenated alcohol).

The performance of the catalyst does not change after an operating time of 4800 hours.

Step (c): Purifying Distillation

The purifying distillation was carried out in a dividing wall column having 30 theoretical plates and a diameter of 80 mm. Montz A3-1000 packings were used as column internals. The column was operated at a pressure at the top of 150 mbar.

The hydrogenated mixture from step (b) was fed in continuously at the side inlet of the column at theoretical stage 14. At the top of the column, the low boilers, mainly HGAC, were separated off and condensed out in the top condenser. The condensed vapors are collected and returned in their entirety to the ketone reservoir for the ethynylation.

The purified HNER was taken off from the dividing wall column as a liquid stream having a purity of 98.5% via a side offtake. At the bottom of the column, temperatures of from 180° C. to 190° C. were reached. At these temperatures, only small amounts of HNER remained in the bottoms. The bottoms were fed to a thin film evaporator operated at 10 mbar to separate off this HNER and the product from the top of the thin film evaporator was returned to the column. The bottoms from the thin film evaporator were discharged from the process.

The weighed total yield of distilled HNER over the steps a) to c) was 91.9% at a selectivity based on HGAC of 92.0%. Together with the details provided in the examples, this shows that the allyl alcohol can be obtained from the corresponding ketone in a technically simple manner at high selectivities and in high space-time yields by means of steps a) to c) of the process of the present invention.

The H-nerolidol obtained in this way can, if desired, be reacted further to produce H-farnesylacetone in a continuous Carroll reaction.

This reaction of an allyl alcohol with an acetoacetic ester is described by way of example for the conversion of H-linalool into H-geranylacetone in the following example.

Step (d): Preparation of H-GAC by Means of a Continuous Carroll Reaction

The apparatus used for the reaction is a fractionation column containing 30 bubble cap trays (about 20 theoretical plates) and having an internal diameter of 30 mm. The trays are numbered from the bottom upward, i.e. the lowermost tray is tray 1 and the uppermost tray is tray 30. The column is provided at regular intervals with thermocouples so that the temperature can be measured both at the bottom and top of the column and at each $3^{rd}$ to $4^{th}$ theoretical plate. In addition to the temperature profile, the concentration profile in the column can be determined with the aid of appropriate sampling points. The vaporizer, which can be heated to 250° C. with the aid of a thermostat, has a volume of about 350 ml, but the fill level during operation is about 225 ml. A condenser operated by means of a cryostat is installed at the top of the column. Furthermore, the column is provided with a vacuum apparatus and a cold trap. All inflowing and outflowing streams are measured with the aid of weighing devices and recorded.

135.0 g/h (0.81 mol/h) of 3,7-dimethyl-1-octen-3-ol (dihydrolinalool) were fed in onto the tray 27 of the column and 94.0 g/h (0.81 mol/h) of methyl acetoacetate were fed in onto tray 3 of the column. As catalyst, use was made of a methanolic solution of a mixed aluminum triacetoacetate prepared by reaction of aluminum sec-butoxide with methyl acetoacetate. The catalyst was characterized by elemental analysis and $^1$H-NMR spectroscopy, which indicated an aluminum content of 5.0% by weight and a degree of transesterification (replacement of methanol by 2-butanol) of 50%. 7.6 g/h (1.5 mol % of aluminum based on methyl acetoacetate) of this catalyst were fed in onto tray 27 together with the 3,7-dimethyl-1-octen-3-ol. A system pressure of 500 mbar and a reflux ratio of 3 were set. The temperature at the bottom was 200° C. and the residence time in the reactor system was 2 hours. As bottoms stream, 171.7 g/h of crude product comprising 87.4% by weight of 6,10-dimethylundec-5-en-2-one, 3.8% by weight of 3,7-dimethyl-1-octen-3-ol, 0.4% by weight of methyl acetoacetate and 8.4% by weight of high boilers were obtained. At the top of the column, 23.3 g/h of distillate comprising 89.5% by weight of methanol were taken off. The carbon dioxide formed during the reaction was discharged at the top. 6,10-Dimethylundec-5-en-2-one was obtained with a selectivity of 99.2% based on 3,7-dimethyl-1-octen-3-ol and 95.4% based on methyl acetoacetate. The conversion was 95% based on 3,7-dimethyl-1-octen-3-ol and 99.2% by weight based on methyl acetoacetate. 6,10-Dimethylundec-5-en-2-one having a purity of 99.99% was obtained from the crude product in a distillation column having 22 theoretical plates.

The example shows that the Carroll reaction can be carried out in a high space-time yield and with high selectivity by means of the process of the present invention.

The ketone obtained in step d) can subsequently be reacted further in step a) (step e)).

We claim:

1. A process for preparing higher, α,β-unsaturated alcohols of the formula Ia

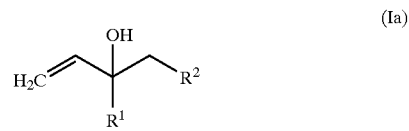
(Ia)

where $R^1$ is a $C_1$–$C_4$-alkyl radical, $R^2$ is hydrogen or a saturated, monounsaturated or polyunsaturated $C_1$–$C_{30}$-alkyl, cycloalkylalkyl or cycloalkyl radical which may each be substituted by $C_1$–$C_4$-alkyl, a) base-catalyzed monoethynylation of a ketone of the formula $R^1$—CO—CH$_2$—$R^2$ in liquid ammonia (NH$_3$/KOH method or NH$_3$/MOR method), where $R^1$ and $R^2$ are as defined above, to the corresponding acetylene alcohol of formula Ib,

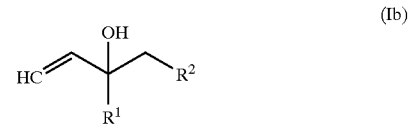
(Ib)

b) subsequent hydrogenation of the acetylene alcohol of the formula Ib in the presence of hydrogen over a Pd-containing thin layer catalyst and c) subsequent purifying distillation of the hydrogenation product and, optionally, d) reaction of the alcohol of the formula Ia

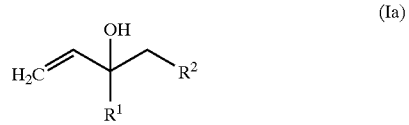

produced in steps a) to c) with diketene or alkyl acetoacetates of the formula IV

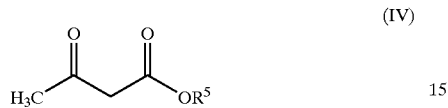

where $R^5$ is $C_1$–$C_4$-alkyl, in the presence of from 0.1 to 0.5 mol % of an organic aluminum compound, based on the alkyl acetoacetate to be reacted, to produce the corresponding methyl ketone extended by 3 carbon atoms, e) and use of the ketone obtained in step d) as starting material for steps a) to c), and wherein only a partial conversion of the ketone is achieved in step a) and the unreacted ketone is separated off in step c) and returned to step a).

2. A process as claimed in claim 1, wherein the partial conversion of the ketone is from 50 to 95%.

3. A process as claimed in claim 1, wherein the reaction of steps a) to c) is followed by a reaction according to steps d) and e).

4. A process as claimed in claim 3, wherein the sequence of steps a) to e) is carried out a plurality of times.

5. A process as claimed in claim 1, wherein the higher alcohols of the formula Ia are selected from the group consisting of
3,7,11-trimethyl-1,6,10-dodecatrien-3-ol (2-NER), 3,7,11-trimethyl-1,6-dodecadien-3-ol (HNER), 3,7,11-trimethyldodec$^{-1}$-en-3-ol (THNER),
3,7,11,15-tetramethyl-1-hexadecen-3-ol (IP), 3,7-dimethylocta-1,6-dien-3-ol (2-LIN), 3,7-dimethylocta-1-en-3-ol (HLIN),
3-methyl-1-(2,6,6-trimethyl-1-cyclohexen-1-yl)penta-1,4-dien-3-ol, and
3-methyl-3-hydroxybutene (MBE).

6. A process as claimed in claim 1, wherein the ketones of the formula $R^1$—CO—$CH_2$—$R^2$ used in step (a) can be used either as pure substances or as mixtures with one another.

7. A process as claimed in claim 1, wherein the ethynylation is carried out in a tube reactor having a CSTR index of greater than 50.

8. A process as claimed in claim 1, wherein the acetylene which has been reacted after a subsection of the reactor in step (a) is replaced by fresh acetylene or by fresh acetylene dissolved in ammonia after this subsection.

9. A process as claimed in claim 1, wherein potassium methoxide in methanol is used as catalyst in step (a).

10. A process as claimed in claim 1, wherein the acetylene alcohols of the formula Ib obtained in step a) can be reacted in the hydrogenation either as pure substances or as mixtures with one another.

11. A process as claimed in claim 1, wherein a short path distillation to separate off high-boiling by-products under gentle conditions is carried out before the fractional distillation of the reaction mixture obtained from steps a) and b).

12. A process as claimed in claim 1, wherein thermally coupled columns are used for the fractional distillation of the reaction mixture obtained from steps a), b) and d).

13. A process as claimed in claim 12, wherein dividing wall columns are used as columns.

14. A process as claimed in claim 13, wherein the dividing wall column is provided with more than one side offtake.

15. A process as claimed in claim 1, wherein the ethynylation of step (a) is carried out using ketones which are obtained by partial or complete selective C═C hydrogenation of 6,10-dimethylundeca-3,5,9-trien-2-one (pseudoionone) or 6,10,14-trimethylpenta-5,9,13-trien-2-one.

16. A process for preparing higher, $\alpha,\beta$-unsaturated alcohols of the formula Ia or Ib

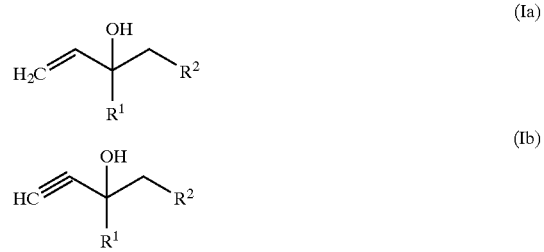

where
$R^1$ is a $C_1$–$C_4$-alkyl radical,
$R^2$ is hydrogen or a saturated, monounsaturated or polyunsaturated $C_1$–$C_{30}$-alkyl, cycloalkylalkyl or cycloalkyl radical which may each be substituted by $C_1$–$C_4$-alkyl, by
a) base-catalyzed monoethynylation of a ketone of the formula $R^1$—CO—$CH_2$—$R^2$ in liquid ammonia ($NH_3$/KOH method or $NH_3$/MOR method), where $R^1$ and $R^2$ are as defined above,
b) optionally, subsequent hydrogenation of the acetylene alcohol of the formula Ib in the presence of hydrogen over a Pd-containing thin layer catalyst and
c) subsequent purifying distillation and, optionally,
d) reaction of the alcohol of the formula Ia or Ib

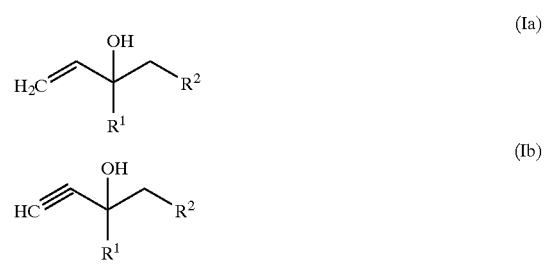

produced in steps a) to c) with diketene or alkyl acetoacetates of the formula IV

where $R^5$ is $C_1$–$C_4$-alkyl,
in the presence of from 0.1 to 0.5 mol % of an organic aluminum compound, based on the alkyl acetoacetate to be reacted, to produce the corresponding methyl ketone extended by 3 carbon atoms, e) and use of the ketone obtained in step d) as starting material for steps a) to c), and wherein only a partial conversion of the ketone of from 50 to 95% is achieved in step a) and the unreacted ketone is separated off in step c) and returned to step a).

17. A process for preparing higher, α,β-unsaturated alcohols of the formula Ia or Ib

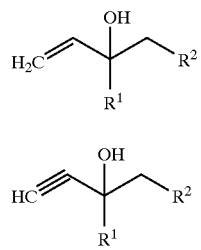
(Ia)

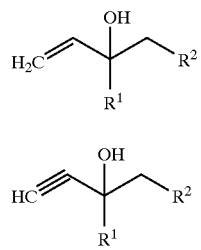
(Ib)

where
$R^1$ is a $C_1-C_4$-alkyl radical,
$R^2$ is hydrogen or a saturated, monounsaturated or polyunsaturated $C_1-C_{30}$-alkyl, cycloalkylalkyl or cycloalkyl radical which may each be substituted by $C_1-C_4$-alkyl, a) base-catalyzed monoethynylation of a ketone of the formula $R^1$—CO—$CH_2$—$R^2$ in liquid ammonia ($NH_3$/KOH method or $NH_3$/MOR method), where $R^1$ and $R^2$ are as defined above, b) optionally, subsequent hydrogenation of the acetylene alcohol of the formula Ib in the presence of hydrogen over a Pd-containing thin layer catalyst and c) subsequent purifying distillation and, optionally, d) reaction of the alcohol of the formula Ia or Ib

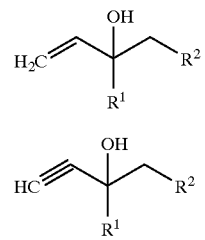
(Ia)

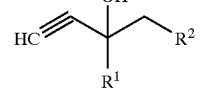
(Ib)

produced in steps a) to c) with diketene or alkyl acetoacetates of the formula IV

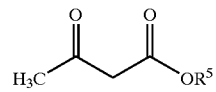
(IV)

where $R^5$ is $C_1-C_4$-alkyl,
in the presence of from 0.1 to 0.5 mol % of an organic aluminum compound, based on the alkyl acetoacetate to be reacted, to produce the corresponding methyl ketone extended by 3 carbon atoms, e) and use of the ketone obtained in step d) as starting material for steps a) to c), wherein only a partial conversion of the ketone is achieved in step a) and the unreacted ketone is separated off in step c) and returned to step a), and wherein thermally coupled columns are used for fractional distillation of the reaction mixture obtained from steps a), b) and d).

* * * * *